United States Patent
Litman et al.

(10) Patent No.: US 11,858,144 B2
(45) Date of Patent: Jan. 2, 2024

(54) METHOD AND SYSTEM FOR AUTONOMOUS BODY INTERACTION

(71) Applicant: Aescape, Inc., New York, NY (US)

(72) Inventors: Eric A Litman, Brooklyn, NY (US); David N. Walsh, Brooklyn, NY (US); Charles Paul Pace, Brooklyn, NY (US); Matthew Dicicco, Brooklyn, NY (US)

(73) Assignee: Aescape, Inc., New York, NY (US)

( * ) Notice: Subject to any disclaimer, the term of this patent is extended or adjusted under 35 U.S.C. 154(b) by 108 days.

(21) Appl. No.: 17/319,064

(22) Filed: May 12, 2021

(65) Prior Publication Data

US 2022/0388168 A1    Dec. 8, 2022

Related U.S. Application Data

(60) Provisional application No. 63/023,839, filed on May 12, 2020, provisional application No. 63/023,833, filed on May 12, 2020.

(51) Int. Cl.
  *B25J 9/16*   (2006.01)
  *A61B 34/32*  (2016.01)
  *B25J 13/08*  (2006.01)

(52) U.S. Cl.
  CPC ............ *B25J 9/1664* (2013.01); *A61B 34/32* (2016.02); *B25J 13/08* (2013.01)

(58) Field of Classification Search
  CPC ......... B25J 9/1664; B25J 13/08; A61B 34/32; A61B 2034/105; A61B 2034/2046; A61B 2034/2055; A61B 2034/2065
  (Continued)

(56) References Cited

U.S. PATENT DOCUMENTS 6,494,851 B1 * 12/2002 Becher ............... A61H 33/6089
                                                          601/134
6,585,668 B2 *  7/2003 Nissim ................. A61H 7/001
                                                          601/134
(Continued)

FOREIGN PATENT DOCUMENTS

CN    203017580 U    6/2013
CN    204684116 U    10/2015
(Continued)

OTHER PUBLICATIONS

David, Pradeep, "Cobots—A helping hand to the healthcare industry," Nov. 24, 2017, Universal Robots, 6 pages.
(Continued)

*Primary Examiner* — Jaime Figueroa
(74) *Attorney, Agent, or Firm* — Van Pelt, Yi & James LLP

(57) ABSTRACT

A system, method, and apparatus for autonomous body interaction system is provided. A system and method for a robot interacting with a human or other soft or deformable body is provided for the purpose of active application of pressure to specific points or regions of the body. The system and method conducts at least one of: localizing the position of the body, detecting the configuration of the body, identifying the surface region(s) of the body, predicting the underlying anatomy of the body, assessing the state of the body, preparing a plan for manipulation of the body, and executing a predetermined and/or dynamically updated plan on the body.

23 Claims, 5 Drawing Sheets

(58) Field of Classification Search
USPC ................ 700/245–264; 318/568.11–568.25
See application file for complete search history.

(56) References Cited

U.S. PATENT DOCUMENTS

| | | | |
|---|---|---|---|
| 6,607,499 B1* | 8/2003 | Becher | A61H 23/0263 |
| | | | 601/103 |
| D517,218 S | 3/2006 | Kalen | |
| D637,304 S | 5/2011 | Feuerabend et al. | |
| D637,305 S | 5/2011 | Feuerabend et al. | |
| D644,675 S | 9/2011 | Abed | |
| D665,093 S | 8/2012 | Sedic | |
| 10,034,813 B1 | 7/2018 | Silver | |
| 10,034,814 B2 | 7/2018 | Zhang | |
| D831,769 S | 10/2018 | Tranchard | |
| D833,028 S | 11/2018 | Olivares et al. | |
| 10,390,755 B2* | 8/2019 | Goodall | A61N 5/0625 |
| D861,829 S | 10/2019 | Wang | |
| D867,609 S | 11/2019 | Couto et al. | |
| 11,197,799 B2* | 12/2021 | Tian | A61H 39/02 |
| 11,338,443 B2 | 5/2022 | Eyssautier | |
| 11,475,630 B2* | 10/2022 | Tian | G06T 19/00 |
| 11,529,900 B2* | 12/2022 | Kim | B60N 2/0244 |
| 11,654,551 B2 | 5/2023 | Huang | |
| 2001/0014781 A1* | 8/2001 | Nissim | A61H 7/001 |
| | | | 601/84 |
| 2002/0013641 A1 | 1/2002 | Nourbakhsh et al. | |
| 2007/0000374 A1 | 1/2007 | Clark et al. | |
| 2007/0192910 A1 | 8/2007 | Vu et al. | |
| 2010/0261530 A1 | 10/2010 | Thomas | |
| 2011/0112549 A1 | 5/2011 | Neubach | |
| 2015/0351999 A1 | 12/2015 | Brouse | |
| 2016/0242995 A1 | 8/2016 | Karkkainen | |
| 2017/0079871 A1 | 3/2017 | Zhang | |
| 2017/0123487 A1 | 5/2017 | Hazra | |
| 2017/0156662 A1* | 6/2017 | Goodall | A61N 2/002 |
| 2017/0258598 A1 | 9/2017 | Radermacher | |
| 2017/0266077 A1* | 9/2017 | Mackin | A61G 13/1235 |
| 2017/0281254 A1 | 10/2017 | Bonutti | |
| 2019/0000447 A1 | 1/2019 | Shelton, IV | |
| 2019/0160684 A1 | 5/2019 | Gu | |
| 2019/0167512 A1 | 6/2019 | Forsythe | |
| 2019/0381271 A1* | 12/2019 | Jo | A61H 15/00 |
| 2020/0055195 A1 | 2/2020 | Ignakov | |
| 2020/0121556 A1* | 4/2020 | Tian | A61H 39/02 |
| 2020/0126297 A1* | 4/2020 | Tian | G06T 7/55 |
| 2020/0206913 A1 | 7/2020 | Kaehler | |
| 2020/0281805 A1 | 9/2020 | Qiu et al. | |
| 2020/0391021 A1 | 12/2020 | Sachs | |
| 2021/0085558 A1* | 3/2021 | Shin | G06V 40/169 |
| 2021/0154852 A1* | 5/2021 | Eyssautier | G05B 19/401 |
| 2021/0155136 A1* | 5/2021 | Kim | B60N 2/0244 |
| 2022/0133589 A1 | 5/2022 | Gruneberg | |
| 2022/0134551 A1 | 5/2022 | Litman et al. | |
| 2022/0387118 A1 | 12/2022 | Litman et al. | |
| 2022/0388165 A1 | 12/2022 | Walsh et al. | |
| 2022/0388168 A1 | 12/2022 | Litman | |
| 2022/0414291 A1* | 12/2022 | Eyssautier | G06F 3/014 |

FOREIGN PATENT DOCUMENTS

| | | |
|---|---|---|
| CN | 206416184 U | 8/2017 |
| CN | 111053530 A | 4/2020 |
| CN | 113908035 A | 1/2022 |
| SG | 10201809094 A1 | 5/2020 |
| WO | WO-2021116554 A1 | 6/2021 |
| WO | WO-2021231663 A3 | 2/2022 |
| WO | WO-2022056181 A1 | 3/2022 |

OTHER PUBLICATIONS

Screen captures from YouTube video clip entitled "Robots can now give full-body personalized massages at home," 11 pages, uploaded Jul. 21, 2020, New Scientist, Retrieved from Internet: https://www.youtube.com/watch?v=t59TXsK1a6c.

Ulanoff, Lance, "Massage Robotics wants you to come and be touched by a robot—if that's your thing," Jan. 6, 2022, Techradar, The source for Tech Buying Advice, 13 pages.

Ex Parte Quayle Action for U.S. Appl. No. 29/732,265, mailed Dec. 2, 2022, 4 pages.

Massage instruments. (Design-©Questel) orbit.com. [Online PDF compilation of references selected by examiner] 17 pgs. Print Dates Range Feb. 24, 2004-Feb. 14, 2020 [Retrieved Nov. 18, 2022] https://www.orbit.com/export/LI CZAH96 B/pdf4/e9bd54bf-4351-4947-8aae-2394fdea7fed-013045.pdf (Year: 2022).

International Search Report and Written Opinion for Application No. PCT/US2021/032111, dated Jan. 24, 2022, 11 pages.

International Search Report and Written Opinion for Application No. PCT/US2021/049741, dated Feb. 7, 2022, 5 pages.

Kraus, Rachel, "Bow down before this $310,000 massage mega-robot, human: Who knew the robot uprising would be so good on the shoulders?," Health & Wellness Artificial Intelligence, Dec. 30, 2021, https://mashable.com/article/massage-robot-.

Hu et al., "A massage robot based on Chinese massage therapy", 2013, Emerald Group Publishing, The Industrial Robot: An International Journal, vol. 40, No. 2, pp. 158-172. (Year: 2013).

Luo et al., "Human Body Trajectory Generation Using Point Cloud Data for Robotics Massage Applications", 2014 IEEE International Conference on Robotics & Automation (ICRA), Hong Kong Convention and Exhibition Center May 31-Jun. 7, 2014. Hong Kong, China, pp. 5612-5617 (Year: 2014).

Meera et al., "Path planning and motion control for a 3 DOF massaging robot," 2016 International Conference on Robotics and Automation for Humanitarian Applications (RAHA), Amritapuri, India, 2016, pp. 1-6, doi: 10.1109/RAHA.2016.7931883. (Year: 2016).

Minyong et al., "Expert massage motion control by multi-fingered robot hand," Proceedings 2003 IEEE/RSJ International Conference on Intelligent Robots and Systems (IROS 2003) (Cat. No. 03CH37453), Las Vegas, NV, USA, 2003, pp. 3035-3040 vol. 3, (Year: 2003).

Si et al., "Green Internet of Things Application of a Medical Massage Robot With System Interruption," IEEE Access, vol. 7, pp. 127066-127077, 2019, doi: 10.1109/ACCESS.2019.2939502. (Year: 2019).

* cited by examiner

METHOD AND SYSTEM FOR AUTONOMOUS BODY INTERACTION

CROSS-REFERENCE TO RELATED APPLICATION(S)

This application claims priority to U.S. Provisional Patent Application No. 63/023,833, entitled METHOD AND SYSTEM FOR AUTONOMOUS OBJECT MANIPULATION, filed on May 12, 2020; and, U.S. Provisional Patent Application No. 63/023,839, entitled METHOD AND SYSTEM FOR AUTONOMOUS BODY INTERACTION, filed on May 12, 2020, and incorporates each of the two aforementioned provisional patent applications in its entirety by reference hereto.

COPYRIGHT AND TRADEMARK NOTICE

Portions of the disclosure in this patent application contain material which is subject to copyright and/or trademark protection. The patent application owner has no objection to the facsimile reproduction of the published patent application or any resulting granted patent, as it appears in the U.S. Patent and Trademark Office records, but otherwise reserves all copyright and trademark rights whatsoever throughout the world.

FIELD OF INVENTION

The present invention relates to a system, method, and apparatus for autonomous body interaction. More specifically, the present invention relates to a system, method, and apparatus for a robot interfacing with soft body tissue.

BACKGROUND OF INVENTION

Robotics have been used for various applications, including assembly manufacturing and device testing. Such robotics have been used to test or manufacture textiles and devices. Other robotics have been used in medical surgery, requiring slow, precise movement. Often, the robotics are controlled in real-time, such as those robotics used in medical procedures, in order to control and monitor the actions of the robotics.

Soft body objects, such as body tissue, may not be uniform in consistency and react to undue pressure differently than similar sized samples, due to the specific characteristics of the unique body tissue sample. Accordingly, available systems and methods for device testing or manufacturing are not configured to handle soft body objects, or their inherent inconsistencies. Likewise, real-time controlled systems and methods for medical procedures are not configured to handle soft body objects in an automated manner.

Accordingly, there exists a need for a robotic handling of soft tissue, potentially nonuniform or nonhomogeneous, in a dynamic or automated system and method.

SUMMARY

Embodiments of the present invention provide for a body interaction system and method, including a robotic arm, the robotic arm having a touch point; a support structure, the support structure configured to have a body disposed thereon; a controller, using a computer processor, the controller providing electronic instructions to the robotic arm to make contact with the touch point to a destination, wherein the destination is configured to be the body.

Embodiments of the present invention further provide for at least one interaction goal, wherein the instructed contact of the touch point with the destination is defined by the at least one interaction goal, and wherein there can be a plurality of interaction goals.

Embodiments of the present invention provide that the at least one interaction goal is one or a sequence of landmarks located on at least one of the surface of the destination, the surface of a deformed destination, and the surface of a compressed destination.

Embodiments of the present invention provide for where at least one of: the touch point is a robotic end effector; and the touch point is a robotic end effector configured to mimic human function. Embodiments of the present invention provide computer readable instructions to make contact are predetermined. Embodiments of the present invention provide that the at least one interaction goal focuses spatially on at least one region of the destination. Embodiments of the present invention provide that a manipulation feedback mechanism, the manipulation feedback mechanism configured to communicate with the controller via the computer processor.

Embodiments of the present invention provide for a body interaction method, including: receiving, by a computer processor, sensor data from a sensor monitoring a body interaction; locating body data from the received sensor data; determining body position and body orientation from the located body data; generating at least one body shape parameter from the located body data; transforming the body data, the body position, the body orientation, and the at least one body shape parameter into a body model; and using the body model, generating a body mapping, wherein the body mappy is configured to be used to generate an interaction protocol. Embodiments of the present invention further provide generating at least one body joint parameter from the located body data, and transforming the at least one body joint parameter into the body model.

Embodiments of the present invention provide the interaction protocol is used to generation an interaction plan, and wherein the interaction plan is used to generation at least one interaction goal used to generate commands executable by a robot device.

Embodiments of the present invention provide for a robotic control system and method, including: maintaining a Finite Element Analysis mechanical model of the body being manipulated based on force sensing, defining position and force states of the controller predicted to cause specific parameter deformations of the model.

Embodiments of the present invention provide for a robotic control system and method utilizing a sensing system to capture the three dimensional structure of the body targeted for manipulation; capturing of the body including its location, pose, configuration, and shape; targeting process including the adaptation of a plan designed for another body re-targeted to the current body through a scaling process; and the scaling process including the adaptation of goals based on proportional region correspondences and body surface orientations.

Embodiments of the present invention provide for a body modeling based on a linear deformation model trained on a large datasheet of sampled individual bodies. A robotic control system and method is provided that digitizes the sensed position and force of the robot while it is under manipulation from a human user or by an automatic method using predetermined parameters and/or interaction goals, who is using the robot to perform body interaction with a body. The digitized position and force readings are encoded into a specific format where the positional goals are combined with force goals such that the two goals can be resynchronized on playback to favor one of the goals over the other in order to adapt to the playback conditions.

DETAILED DESCRIPTION

The various embodiments described and illustrated are for the purpose of showing some example embodiments of the present invention and are not intended to limit in any way the scope of the present invention.

Figure 1:
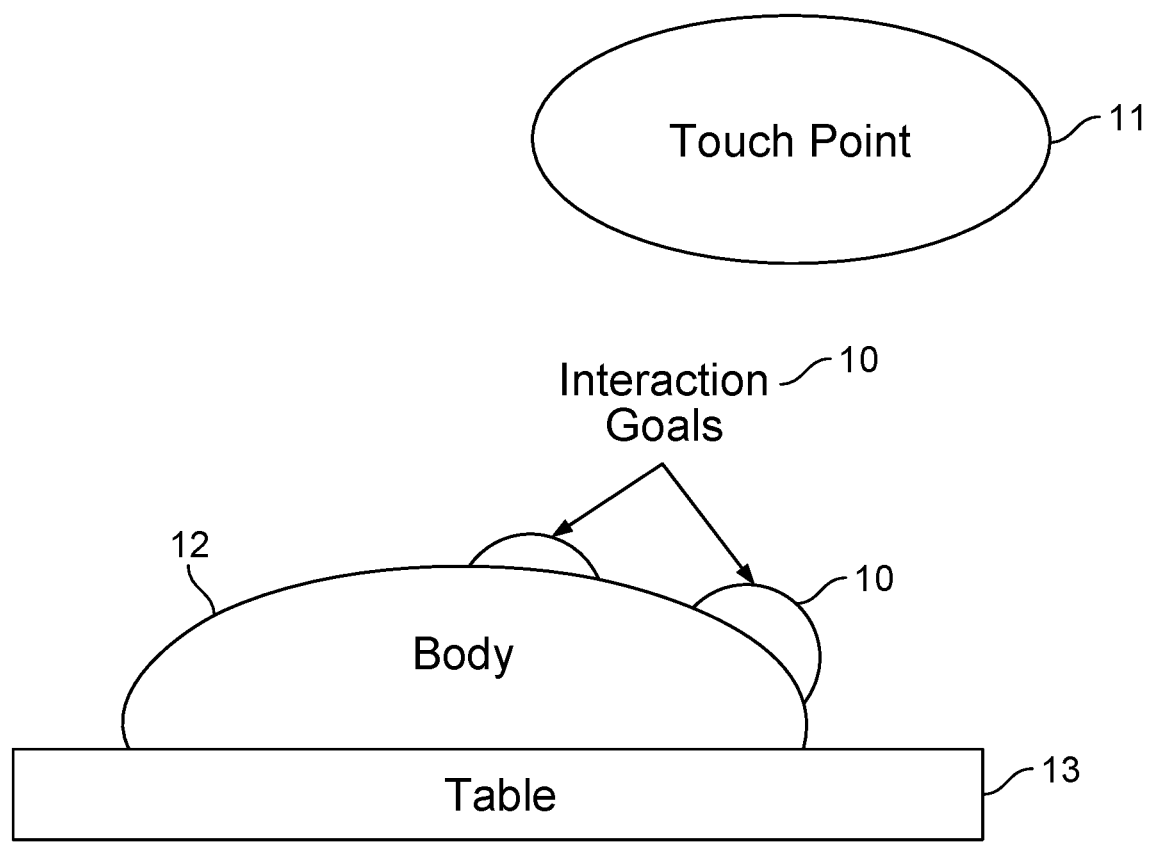
FIG. 1 shows a body interaction system according to an embodiment of the present invention.

In embodiments of the present invention, a system, method, and apparatus for autonomous body interaction system is provided. A system and method for a robot interacting with a human for the purpose of active application of pressure to specific points or regions of the human body. In an embodiment, the object manipulation system as shown in FIG. 1 is utilized. In embodiments, the system and method effects one or more of the following: localizes the position of the body (human or otherwise), detects the configuration of the body, identifies the surface regions of the body, predicts the underlying anatomy of the body, assesses the state of the body, plans manipulation of the body, and executes a predetermined and/or dynamically updated plan on the body. In embodiments, the system and method effects the following: localizes the position of the body (human or otherwise), detects the configuration of the body, identifies the surface regions of the body, predicts the underlying anatomy of the body, assesses the state of the body, plans manipulation of the body, and executes a predetermined and/or dynamically updated plan on the body.

In embodiments, a system, method, and apparatus provide for a therapeutic massage plan applied by a robot with one or more arms, to the body of a human lying prone, face down, on a massage table. The robot arm(s) are positioned to the side of the table such that the workspace reach of each robot arm substantially covers the target regions of the therapeutic massage. In an embodiment, the mounting position of the robot arm(s) is determined to maximize the pressure application required for the therapeutic massage. In embodiments, the therapeutic massage or other plan can be effected on the front region or a side or other region of a body. In embodiments, the therapeutic massage or other plan can be effected on a body which is human, mammal, animal, or a non-living object. In embodiments, the therapeutic massage or other plan can be effected on non-living soft body objects.

In an embodiment, the therapeutic massage plan includes effecting one or more interaction goals which are manipulation goals that specify additional data relevant to the manipulation and interaction with a body. The additional data included in the interaction goals includes, without limitation: light contact along the surface of the skin, moderate pressure contact to somewhat displace the skin from the subcutaneous fascia, higher pressure contact to displace, compress, and mobilize muscle tissue, and higher pressure contact to mobilize deeper tissue and skeletal structures. Additional data can be included. In embodiments, overlays can be added to these interaction goals which have additional changes in position or force that vary in time around a mean value of zero. Such overlays can inject additional therapeutic effects to an interaction goal which does not normally have it. Example overlay effects include: varying the position of goals in a plane parallel to the surface of the target body in a sinusoidal manner in a direction perpendicular to the target's muscle fiber (known as the cross-fiber direction), in a direction parallel to the muscle fiber, or in a circular manner; or varying the force goals in a sinusoidal manner in a direction normal to the target body (also referred to as percussive force or percussive force overlay).

In embodiments, when manipulating soft objects, the additions to the controller allow for a mixture of goals to be desired and achieved in a way similar to what humans are capable of achieving. These goals are extended into complex plans that are focused on a therapeutic outcome. The complexities in terms of object manipulation and object modeling increase when considering a living body such as a human body versus any soft object. In embodiments, there is a tracking of the body as it moves and the system and method are configured to perform manipulation on the body while the body is in motion, maintaining contact with the body as it moves on its own and as the robot or tool causes it to move.

In an embodiment, the table (or work table or surface) under the body or object is able to articulate the different parts of the body independently. Throughout the specification, the surface or structure supporting the body or object is referred to as "table" for ease of reference in embodiments but is not meant to be limited to a table. The supporting structure or surface can be the ground, a chair or other furniture, a highly adjustable table, or other structure or means of support.

In an embodiment, the supporting structure or table includes handles that the user can grip with their hands. In an embodiment, the body interaction manipulation is configured to provide traction relative to the hand that is fixed in place holding the handle of the table.

In an embodiment, the supporting structure or table includes stirrups into which the user can insert their feet. In an embodiment, the body interaction manipulation is configured to provide traction to the foot that is fixed in place and inserted into the stirrup.

In an embodiment, the handle(s) are associated with the robot and the robot controls the interaction of the user's grip on the handle. For the hand that is holding the handle attached to the robot, the body interaction manipulation provides resistance and mobilization to the hand, arm, and shoulder. Force feedback is used to assess the resistance and add resistance for the user's body. The robot moves the user's hand, arm, and shoulder through a range of motion until there is resistance that reaches a predetermined or dynamic threshold.

In an embodiment, the robot includes stirrups into which the user can insert their feet. For the foot that is in the stirrup attached to the robot, the body interaction manipulation provides resistance and mobilization to the foot, leg, and hip. Force feedback is used to assess the resistance and add resistance for the user's body. The robot moves the user's foot, leg, and hip through a range of motion until there is resistance that reaches a predetermined or dynamic threshold.

FIG. 1 depicts the body interaction system, primarily comprising a touch point 11, a body 12 and a table 13. The body's volume and weight are supported by the table while the system moves the touch point into contact with and along the body. In an embodiment, the planned contact of the touch point with the body is defined by a plurality of interaction goals 10.

In an embodiment, the body is a human body. In an embodiment, the touch point is a robotic end effector specifically designed to mimic the hands, fingers, palm, forearm, and/or elbow of a human in form and function.

In an embodiment, a body, soft body object or object, is lying on or supported by a flat surface or worktable 14. At least one robot arm with at least one end effector or tool is employed. The worktable provides support for the body/object and the tool which acts upon the body/object. The tool moves through freespace and into physical contact with the object. Such contact between the tool and the body/object can be predetermined or planned through a plurality of specified manipulation goals or sequences of specific types of contact or pressure.

In an embodiment, the interaction goals are a sequence of landmarks, both on the surface of the body and inside the body in close proximity to the surface. When the interaction goals are inside the body, this is a position that is achieved through deformation of the body, where the position is on the surface of the deformed or compressed body. The positioning of these interaction goals and the resulting deformation or compression of the body required to achieve these positions is associated with a specified beneficial change in the state or condition of part of the body or the whole of the body.

In an embodiment, the interaction goals focus spatially on regions of the skin that are reliably correlated to underlying tissue properties. Examples of tissue properties include those associated with unwanted tension, adhesions, and trigger points. The manipulation of these tissue properties is generally associated with a positive change in the tissue state, including the release of unwanted tension, loosening of adhesions between tissue layers, and reflexive smoothing of muscles when stimulating specific nerves.

In an embodiment, the targeting and the planning progress from easily-identifiable anatomical features to less-defined features and "hidden" features such as features within the body (e.g., bone structure, sensitivities, etc.). These techniques rely upon the feedback mechanism of manipulating the body while also recording new sensed information resulting from that manipulation. In an embodiment, the method and system include manipulation feedback mechanism with a robot control system that has a dynamic contact point or patch.

Figure 2:
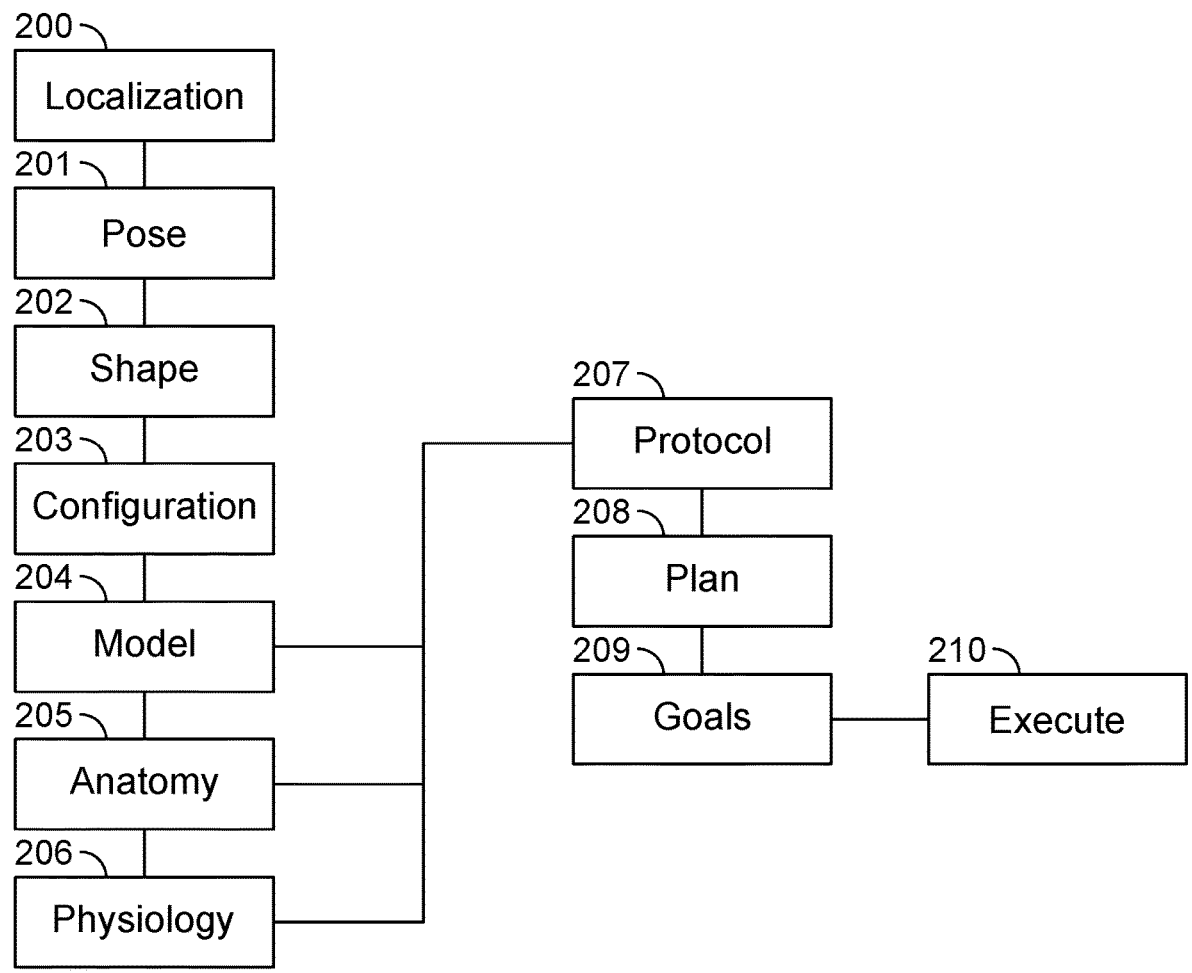
FIG. 2 shows a body interaction method according to an embodiment of the present invention.

FIG. 2 shows a body interaction procedure according to an embodiment of the present invention. In FIG. 2, the localization step 200 locates and segments the body data in the sensed data. In an embodiment, the system and method can assign object labels for ease of reference and recording. In FIG. 2, the pose step 201 determines the body position and body orientation. The shape step 202 estimates the body shape parameters based on the body data. The configuration step 203 estimates the body joint pose parameters based on the body data. In the model step 204, the body data, body shape, and body joint pose are combined into a body model. In the anatomy step 205, the body model is registered with an anatomical model to generate the anatomical mapping. In the physiology step 206, the sensed physiologic signals of the body are related to the body model through a physiologic mapping. In the protocol step 207, the body model, anatomical mapping, and physiologic mapping are utilized to generate the interaction protocol.

In the plan step 208, the interaction protocol is used to generate the interaction plan. In the goal step 209, the interaction plan is used to generate the interaction goals. In the execute step 210, the interaction goals are used to generate commands executed by the robot.

In an embodiment, the localization step is implemented with a deep learning model trained to assign object labels to sensed data associated with a body. A further embodiment utilizes sensed RGB-D (red, green, and blue color-depth sensing) data from one or more sensors. RGB-D sensors work in association with an RGB sensor camera and are able to augment a convention image with depth information on a per-pixel basis.

In an embodiment, the pose step is implemented with a deep learning inference model that detects the body's joint poses and semantically segments the sensed data, classifying data as body data. In an embodiment, the shape step and configuration step are performed jointly by fitting model parameters for both pose and shape. In an embodiment, the configuration step is implemented with a deep learning pose estimator.

In an embodiment, the model step is implemented as a finite element analysis (FEA) model generated based on the body shape determined in the shape step. In an embodiment, the anatomy step utilizes a morphable anatomical body model that utilizes surface landmarks from the fitted model to spatially transform the anatomical body model. In an embodiment, the physiology step utilizes thermographic imagery to estimate the blood flow and oxygenation of parts of the body. In an embodiment, the physiology step utilizes a sensed force from sensors in the robotic arms to estimate the relative stiffness of parts of the body.

The embodiments described herein are extensions of and improvements on soft object manipulation, allowing for the complexity of handling a living body. In an embodiment, an extension is an adaptation of the plan to the specific morphology of a body and consideration for its pose and articulation.

In an embodiment, the protocol step has the user select from a variety of available protocols. Each protocol defines interaction segments. Interaction segments are defined by a set of interaction goals. In an embodiment, the system and method can occur with the following steps, and their subsequent metadata, in this order: the regions where the goals are located, the level of force, the duration, the style, and a generalized intensity level. The output of this embodiment is an ordered sequence of segment specifications, which can then be modified by a user. In an embodiment, the system and method can occur with the following steps (the order of which can change or steps removed): the regions where the goals are located, the level of force, the duration, the style, and a generalized intensity level.

In an embodiment, a stroke segment is defined as a sequence of interaction goals. In an embodiment, a stroke specification is defined as a sequence of interaction goals. In an embodiment, the plan step has the user make modifications to the protocol before the protocol is executed to select or generate final interaction goal sets. Modifications would include modifications to any of the individual metadata associated with a stroke specification, or elimination of entire stroke segments based on users preferences. In an embodiment, once modification(s) are made and finalized, the system iterates over each of the stroke segments and either selects a matching prerecorded stroke segment from a database or generates a new stroke segment through an online automated strike segment generation process, using the metadata as input. Additional goals are inserted in between the selected or generated stroke segments to produce one continuous trajectory for execution. This output is referred to as the interaction plan or the plan.

In an embodiment, the execute step involves the user beginning the execution process through an indicator in the user interface (UI). The interaction plan is executed by collecting the parameters associated with the requirements on the UI and sending individual goals to the controller at the appropriate time indicated with each goal. During execution, the user has additional controls to either modify parameters of the body mapping, including to adjust for poor alignment and/or to modify the future segments of the plan. In an embodiment, body model adjustments do not alter the individual goals, but do modify the way that the individual goals are transformed by the controller at time of execution. Adjustments to the plan, e.g., skipping, repeating, extending and/or shortening segments within the plan, adjust the execution of the plan by making adjustments to the remaining unexecuted portion of the plan.

In embodiments, the way in which the protocols are defined allows a mixing of different protocols together simultaneously and sequentially while also able to maintain continuity and achievability for the underlying robotic goals.

Figure 3:
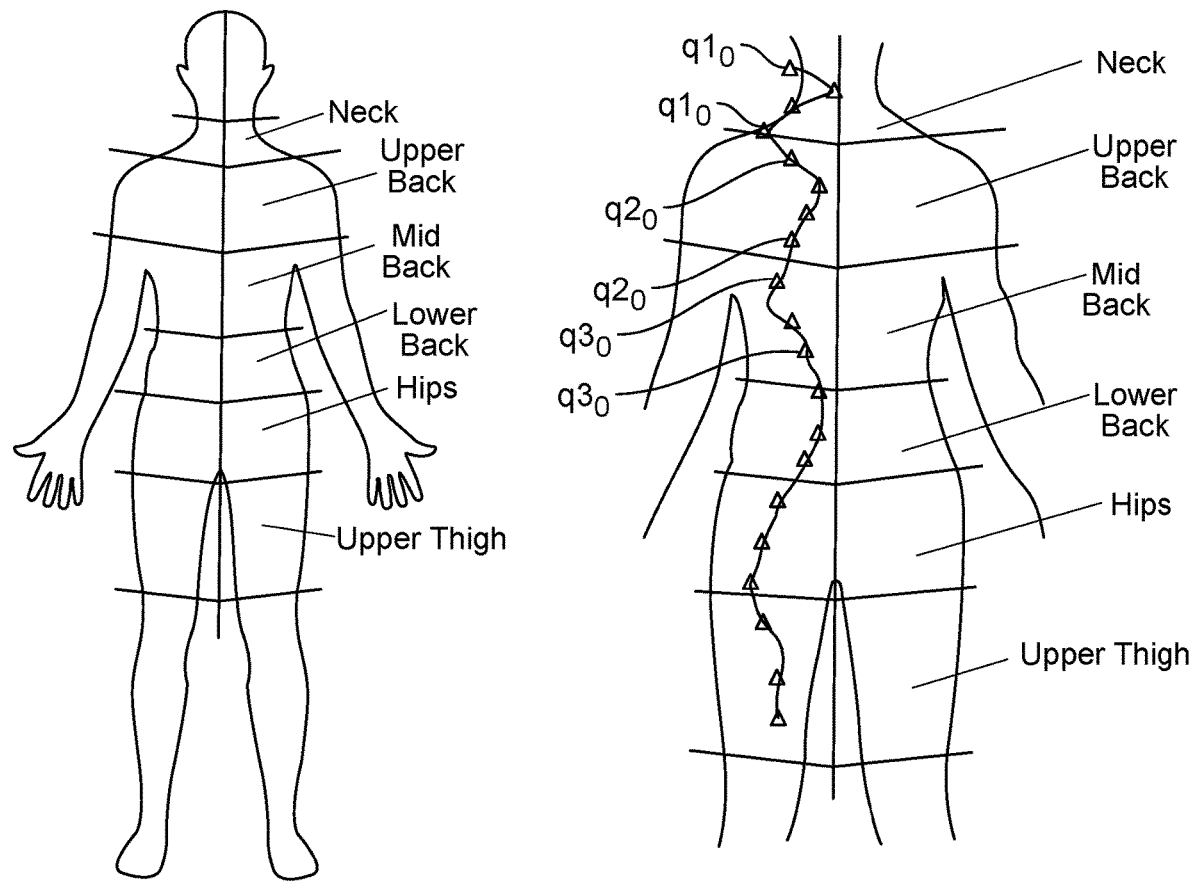
FIG. 3 shows a body mapping model according to an embodiment of the present invention.

FIG. 3 shows a layout of a body mapping. In FIG. 3, multiple regions are defined along the illustrated body from the neck to the upper thigh. This constitutes a basic set of regions for a user lying face down where a stationary set of arms is mounted alongside the table, near the body's shoulder. Within these regions, segments of trajectories (q1, q2, q3, etc.) are displayed within the regions, having time sequences of goals ($q_{i.0}$ to $q_{i.n}$ for segment n). These segments are essentially "chained" together via interpolation along the body's surface to generate a final manipulation plan.

In an embodiment, the body mapping is defined by a set of regions including: the neck, the upper back, the mid back, the lower back, the hips, and the upper thigh. In a further embodiment, regions for the arms and legs are included as well, covering the whole body. In an alternate embodiment, different regions can be defined for the body mapping.

In an embodiment, the body mapping includes specification of goals that are on the skin and below the surface of the skin. Goals with position elements close to the skin generally correspond to low force goals used in more gentle styles of massage. Goals with positions below the skin are generated by the application of large forces, as the force component deforms the surface of the subject based on a bulk elastic behavior of the body tissue.

In an embodiment, the body mapping is defined as a set of region boundaries offset from anatomical positions including an absolute or relative offset from the spine in order to target the erector spinae muscle group.

In an embodiment, the body mapping is used to modify the plan based on model characteristics. Before the execution of the plan, the user has the ability to select the different regions of the body mapping to indicate a desire for more/less force and total duration of time spent within that region. The different segments of the plan can be then modified to either scale or cap their forces, increase or decrease their duration (by decreasing or increasing velocity), or eliminating the segments entirely. Alternatively, an automatic selection can be preset and can occur according to the present plan.

In an embodiment, the body mapping is defined relative to body landmarks, including: the spine, the iliac crest, the hips, the T-3 spinous processes, the clavicle, the inferior angle of the scapula, the C-7 vertebra, the T-3 vertebra, the T-7 vertebra, the L-4 vertebra, the erector spinae group, the trapezius, the rhomboids, and the nuchal furrow.

In an embodiment, the body mapping relates the body landmarks through a geometric transform. In an embodiment, the geometric transform is a three dimensional projective transform accounting for a uniform scaling of the distance between the body landmarks to account for transforming goals from one target subject to another.

In an embodiment, the body mapping utilizes the detected anatomical skeletal joint positions along with detected body shape to relate goals from one individual subject to another.

In an embodiment, the body mapping is performed in an autonomous manner. The perception system detects the body of the subject, segments the points associated with the subject into the subject point cloud. The perception system detects the pose of the subject, including the configuration of the subject's skeletal joints.

The human body is not only a soft object, but its surface topology is complex, with many folds and features, that can be challenging when trying to predict and treat. The various control system embodiments described herein are able to manage progressing along this complex surface, and the body mapping system embodiments described herein allow for better adaptation to a variety of features and situations. Such features and situations can include excessive folding of clothing, various body types, uneven positioning of the body, disability of the body requiring an unconventional positioning, heightened sensitivities of specific body regions or types of contact by the touch contact or end effector, among others.

Figure 4:
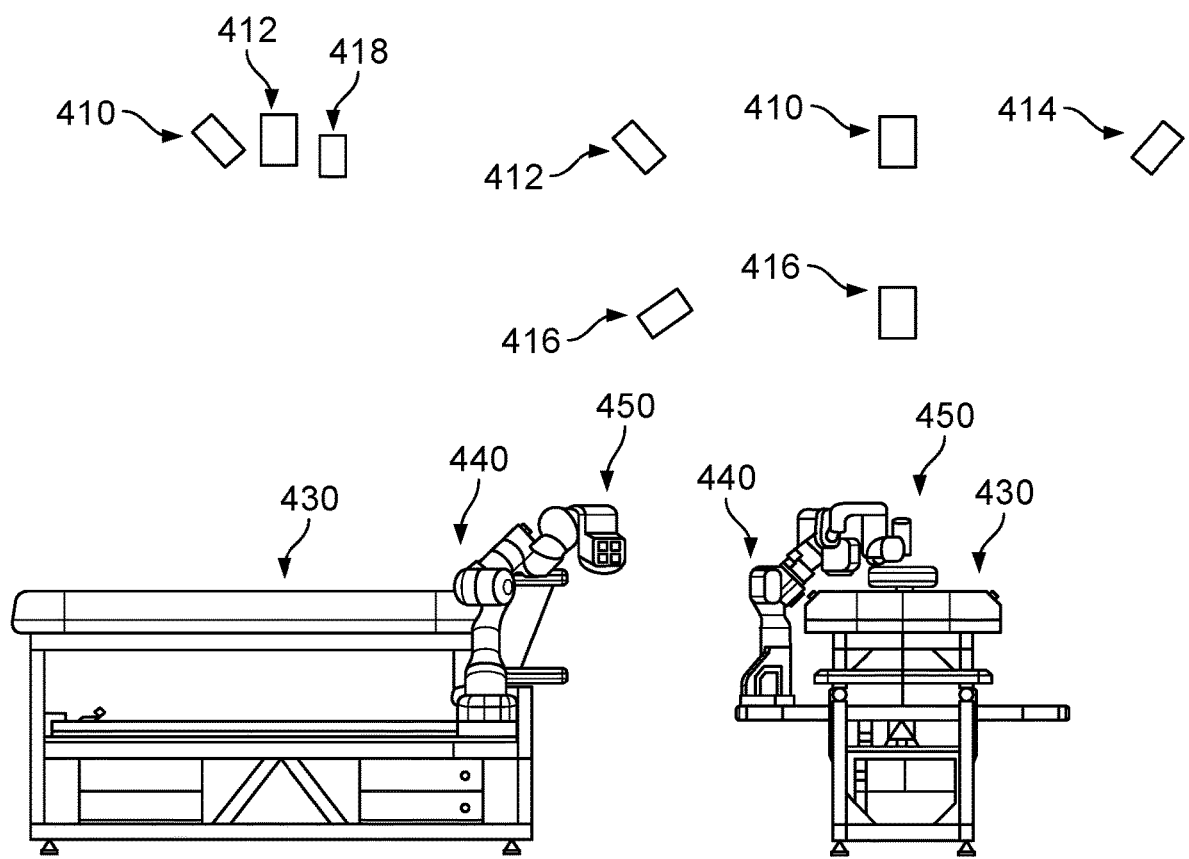
FIG. 4 shows an example system according to an embodiment of the present invention.

FIG. 4 shows a robotic system's vision components situated above and in front of the robot. These components are a way the system senses the body to be manipulated, providing the data that is resolved into a model of the body. Several sensors 410, 412, 418, 414 are arranged above the table 430 and arranged such that when their data is combined they have both a more complete and more validated view of the body. These sensors can be configured to generate thermographic imagery, visible light imagery, infrared imagery, and 3D range sensing. The robot arm 440 is shown attached to the table, and the robot manipulator's end effector tool (450) is at one end of the arm, and at the other end, the robot is attached to the table 430.

Figure 5:
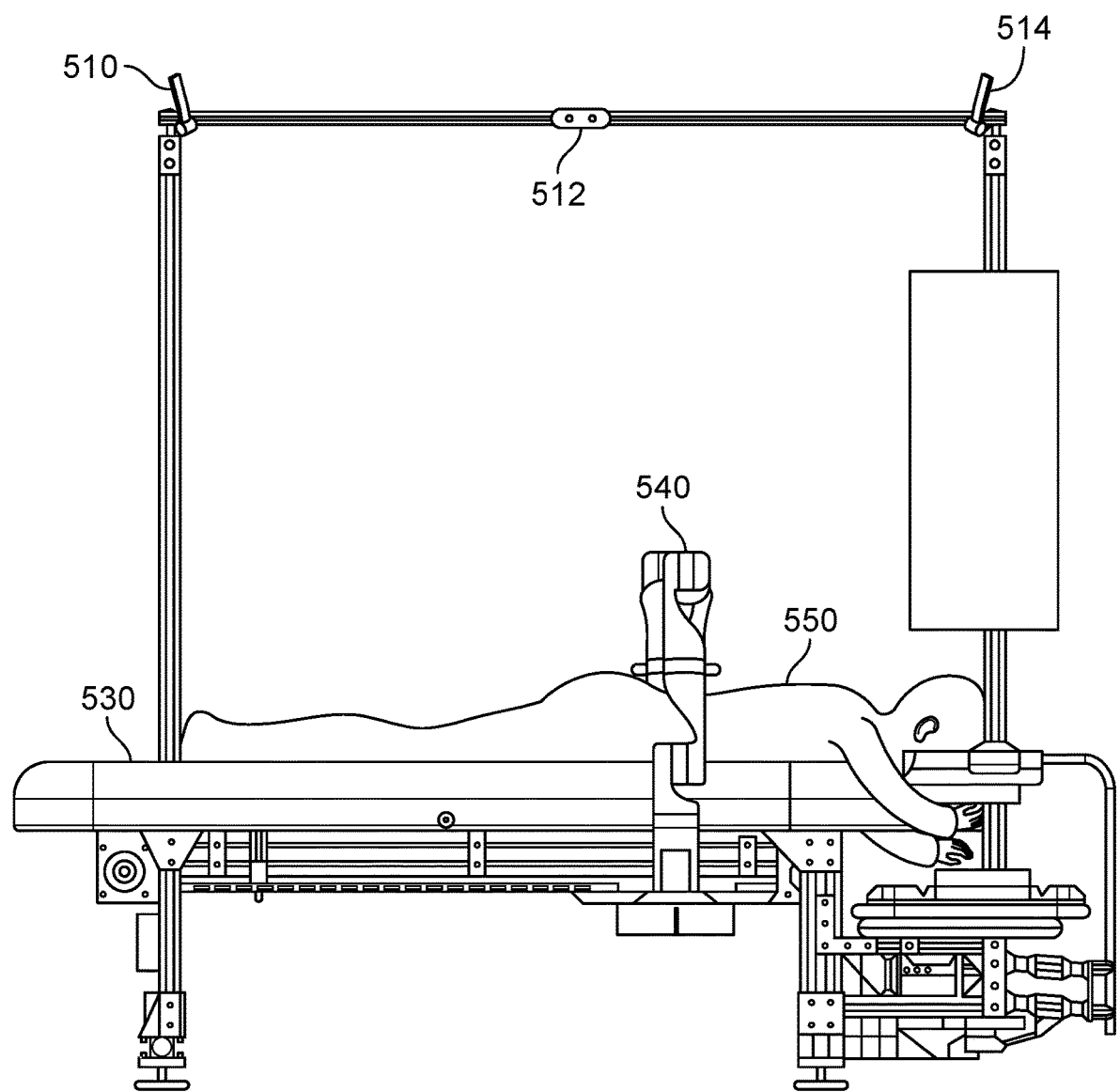
FIG. 5 shows an example system according to an embodiment of the present invention.

FIG. 5 shows a robotic system with a body 550 as the object being targeted for manipulation. The robot arm 540 is shown in contact with the body 550, and the other end of the arm is shown attached to the table 530. Also depicted are sensors 510, 512, 514 mounted above the table 530 such that the sensor's frustums provide a redundant and comprehensive view of the body 550 on the table 530.

In an embodiment, the interaction protocol contains a manipulation protocol that defines manipulation goals. The manipulation goals are generated by an interaction teaching system.

In an embodiment, the interaction teaching system digitizes the manual manipulation of a robot arm that includes a handle in the end effector assembly. The digitization records the position, orientation, and force being applied to a surface by the touch point. It is assumed that the contact force is purely force based, as there is no rigid connection with the touch point and the subject that would allow for torque to be transferred, however since the force/torque sensor is mounted remotely from the point of contact (at the robot wrist), there will be a measured torque moment. The torque moment of the external force measurement is used to calculate the most likely contact point of the touch point.

In an embodiment, the interaction teaching system perceives structural disturbances in the body. These structural disturbances are encoded along with the manipulation goals. The disturbances are noted as special cases for which progression management strategies are formulated. In a further embodiment, a progression management strategy involves the transient relaxation of pressure to allow the touch point to move over the region containing a similar structural disturbance.

In an embodiment, the interaction teaching system utilizes manual manipulation to encode complex maneuvers around body parts. When these maneuvers are played back, the motion dynamics are scaled spatially from the source body in the recording to the target body being played back.

In an embodiment, the robot itself is a recording mechanism that is able to digitize and replicate or "play back" the complex motions and intentions of a human operator, still adapting using the body mapping and control embodiments described herein to the specific constituency and state of a body that is different from the state of a body on which the digital replication or recording was made.

In an embodiment, the overlay effects include modulation based on an auditory signal, music, or bass.

Embodiments of the robot control include a computer or processor controlled system in which programmable actions or steps are coded via computer software program and used to tell or control the movements of the robot control. Embodiments of the programmable instructions to control the robot or robot arm or robot arm with an end effector can be effected by a predefined set of instructions, a machine learning set of instructions in which the system receives feedback from the sensors of the robot to modify pressure, frequency of touch, and other characteristics (e.g., cold, warmth, etc.).

Features of the various embodiments of the above-identified system and method described herein can be modeled and/or effected and/or controlled by a general computer, special purpose computer, a processor, and a smart device having a processor. Embodiments of the method instructions can be stored on a computer-readable medium, the medium being virtual or hardware or portable or in the cloud/networked, having instructions thereon which are readable or can be made to be readable by a computer or processor so that the computer software instructions can be executed. The various embodiments described herein, and those equivalents thereto, can be used for a variety of nonanalogous objects, e.g., human body, animal body, soft body having deformable characteristics, a nonhomogenous body having soft and hard features. The various embodiments described herein, and those equivalents thereto, can be used for massage applications, sensing applications, modeling applications, and others.

The modifications listed herein and other modifications can be made by those in the art without departing from the ambit of the invention. Although the invention has been described above with reference to specific embodiments, the invention is not limited to the above embodiments and the specific configurations shown in the drawings. For example, some components shown can be combined with each other as one embodiment, and/or a component can be divided into several subcomponents, and/or any other known or available component can be added. The processes are not limited to those shown in the examples. Those skilled in the art will appreciate that the invention can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

What is claimed is:

1. A system, comprising:
   a support structure;
   a robotic manipulator including an end effector;
   a controller operably coupled to the robotic manipulator and configured to control an interaction between the end effector and a deformable body when the deformable body is positioned on the support structure; and
   a plurality of sensors positioned to detect, during use, multi-dimensional data associated with the deformable body when the deformable body is positioned on the support structure,
   the controller configured to:
      determine, based on the multi-dimensional data, at least one of a position, an orientation, or a shape of the deformable body when the deformable body is positioned on the support structure;
      generate a body model for the deformable body based on the at least one of the position, the orientation, or the shape of the deformable body;
      generate an interaction plan based on the body model, the interaction plan comprising a time sequence of interaction goals, wherein planned contact of the end effector with the deformable body is defined by the time sequence of interaction goals, and wherein the time sequence of interaction goals defines a trajectory associated with at least a portion of a stroke; and
      cause the robotic manipulator to execute the interaction plan comprising the time sequence of interaction goals, wherein individual interaction goals are sent to the controller based at least in part on a time indicated with each interaction goal.

2. The system of claim 1, wherein the controller is further configured to:
   perform tracking of a movement of the deformable body during execution of the interaction plan; and
   modify the interaction plan based on the tracking, to at least one of maintain contact with the deformable body, or position the end effector relative to a predefined part of the deformable body.

3. The system of claim 1, wherein the interaction plan specifies at least one overlay, the at least one overlay including at least one of a variation of a position goal or a variation of a force goal.

4. The system of claim 1, further comprising assigning labels to the multi-dimensional data using a deep learning model.

5. The system of claim 1, wherein the deformable body is a human body and the planned contact between the end effector and the deformable body includes contact sufficient to at least one of displace, compress, or mobilize muscle tissue within the human body.

6. The system of claim 1, wherein the body model is a current body model, the generating the current body model including modifying a historical body model based on the multi-dimensional data.

7. The system of claim 1, wherein the interaction plan is a current interaction plan, and the generating the current interaction plan includes adjusting a historical interaction plan based on the multi-dimensional data.

8. The system of claim 1, wherein the multi-dimensional data is a first multi-dimensional data, the controller further configured to:
determine second multi-dimensional data based on signals received from the plurality of sensors during the execution of the interaction plan; and
modify the interaction plan during the execution of the interaction plan based on the second multi-dimensional data.

9. The system of claim 8, wherein modifying the interaction plan includes at least one of modifying a pressure of the interaction plan or modifying a frequency of touch of the interaction plan.

10. The system of claim 1, wherein the deformable body is a human body and the support structure includes stirrups configured to accommodate feet of the human body when the deformable body is positioned on the support structure.

11. The system of claim 1, wherein the deformable body is a human body and the support structure includes handles configured to support hands of the human body when the deformable body is positioned on the support structure.

12. A method, comprising:
receiving, at a processor and from a plurality of sensors, sensor data associated with a deformable body in a prone position;
determining, via the processor and based on the sensor data, at least one of a position, an orientation, or a shape of the deformable body in the prone position;
generating, via the processor, a body model for the deformable body based on the at least one of the position, the orientation, or the shape of the deformable body;
generating, via the processor, an interaction plan based on the body model, the interaction plan comprising a time sequence of interaction goals, wherein planned contact of an end effector of a robotic manipulator with the deformable body is defined by the time sequence of interaction goals, and wherein the time sequence of interaction goals defines a trajectory associated with at least a portion of a stroke; and
causing the robotic manipulator to execute the interaction plan comprising the time sequence of interaction goals, wherein individual interaction goals are sent to a controller operably coupled to the robotic manipulator based at least in part on a time indicated with each interaction goal.

13. The method of claim 12, further comprising:
receiving, at the processor and during the execution of the interaction plan, a representation of a user-selected adjustment, the user-selected adjustment including one of: a command to skip a segment of the interaction plan, a command to repeat a segment of the interaction plan, a command to extend a duration of a segment of the interaction plan, or a command to shorten the duration of the segment of the interaction plan.

14. The method of claim 12, wherein the interaction plan is a current interaction plan, and the generating the current interaction plan includes adjusting a past interaction plan based on the sensor data.

15. The method of claim 12, further comprising estimating a subcutaneous anatomy of the deformable body, wherein the generating the interaction plan is further based on the estimated subcutaneous anatomy of the deformable body.

16. The method of claim 12, wherein the plurality of sensors includes at least one camera.

17. The method of claim 12, wherein the sensor data includes at least one of thermographic imagery, visible light imagery, infrared imagery, or three-dimensional range data.

18. The method of claim 12, wherein the end effector is configured to mimic at least one of a form or a function of a human hand.

19. The method of claim 12, wherein the end effector is configured to mimic at least one of a form or a function of a human finger.

20. The method of claim 12, wherein the end effector is configured to mimic at least one of a form or a function of a human forearm.

21. The method of claim 12, wherein the interaction plan includes a plurality of predefined stroke segments.

22. The method of claim 12, wherein the causing the robotic manipulator to execute the interaction plan is in response to an input received via a user interface.

23. The method of claim 12, further comprising identifying a projected contact point of the end effector relative to the deformable body, based on a torque moment of an external force measurement.

* * * * *